United States Patent [19]

Whigham

[11] Patent Number: 4,692,719
[45] Date of Patent: Sep. 8, 1987

[54] COMBINED PACEMAKER DELTA MODULATOR AND BANDPASS FILTER

[75] Inventor: Robert H. Whigham, Aurora, Colo.

[73] Assignee: Telectronics N.V., Curacao, Netherlands Antilles

[21] Appl. No.: 891,478

[22] Filed: Aug. 1, 1986

[51] Int. Cl.⁴ .......................................... H03K 13/22
[52] U.S. Cl. .................................... 332/11 D; 375/28
[58] Field of Search .............. 332/9 R, 11 D; 375/22, 375/23, 27–32; 340/347 AD

[56] References Cited

U.S. PATENT DOCUMENTS

| 4,433,311 | 2/1984 | Noguchi et al. | 332/110 |
| 4,527,133 | 7/1985 | Money | 332/110 |

Primary Examiner—Eugene R. LaRoche
Assistant Examiner—Robert J. Pascal
Attorney, Agent, or Firm—Gottlieb, Rackman & Reisman

[57] ABSTRACT

A combined pacemaker delta modulator and bandpass filter which requires only one active device. The sense signal is applied through a conventional delta modulator capacitor to the minus input of a differential amplifier, and the conventional current sources are connected to the minus input. Instead of simply connecting the plus input to a reference potential, however, it is also coupled, through a resistor, to the input signal, and an RC network is connected across the two inputs.

7 Claims, 6 Drawing Figures

FIG. 4

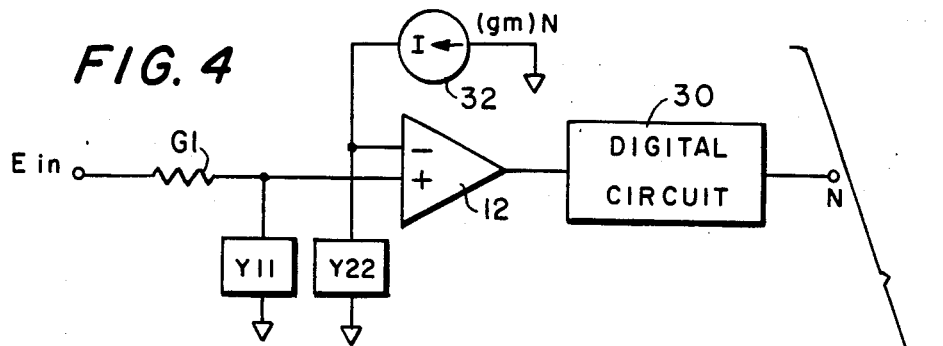

$$\frac{(gm)N}{Y22} = \frac{(Ein)(G1)}{G1+Y11}$$

$$N = \left(\frac{Ein}{gm}\right)\left(\frac{(G1)(Y22)}{G1+Y11}\right) = \left(\frac{Ein}{gm}\right)\left(\frac{(G1)(G2)(sC)}{(G1)(G2+2sC)+s^2C^2}\right) = \left(\frac{Ein}{gm}\right)\left(\frac{sC}{[1+2sC(R2)]+[s^2C^2(R1)(R2)]}\right)$$

FIG. 5

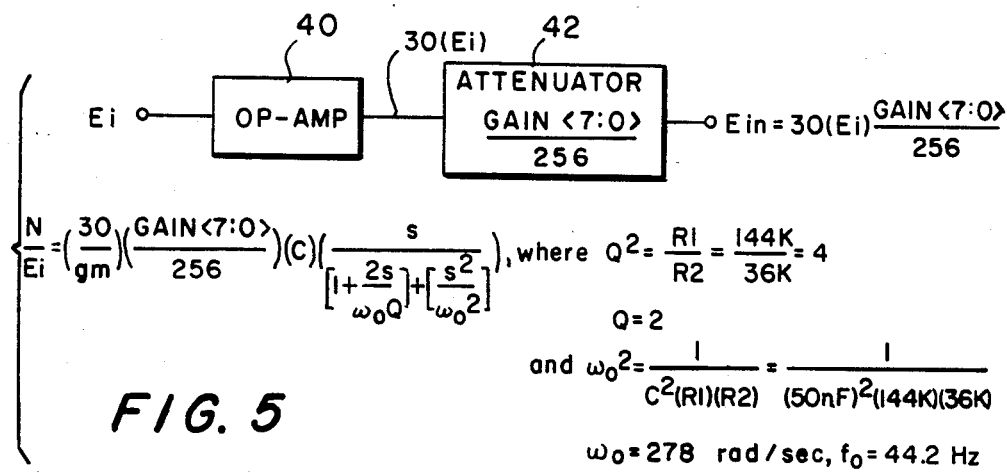

$$\frac{N}{Ei} = \left(\frac{30}{gm}\right)\left(\frac{GAIN\langle 7:0\rangle}{256}\right)(C)\left(\frac{s}{\left[1+\frac{2s}{\omega_0 Q}\right]+\left[\frac{s^2}{\omega_0^2}\right]}\right), \text{ where } Q^2 = \frac{R1}{R2} = \frac{144K}{36K} = 4$$

$$Q = 2$$

$$\text{and } \omega_0^2 = \frac{1}{C^2(R1)(R2)} = \frac{1}{(50nF)^2(144K)(36K)}$$

$$\omega_0 = 278 \text{ rad/sec}, \; f_0 = 44.2 \text{ Hz}$$

FIG. 6

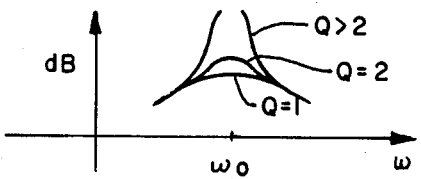

Since $\frac{s^2}{\omega_0} = -1$ when $s = j\omega_0$, the sinusoidal gain at the center frequency is $$\frac{N}{Ei} = \left(\frac{30}{gm}\right)\left(\frac{GAIN\langle 7:0\rangle}{256}\right)\left(\frac{sC}{2sC(R2)}\right) = \left(\frac{30 \text{ counts}}{3.125 \text{ nA}}\right)\left(\frac{GAIN\langle 7:0\rangle}{256}\right)\left(\frac{1}{2(36K\Omega)}\right)$$

$$\frac{N}{Ei} = 520 \; GAIN\langle 7:0\rangle \text{ counts/volt} = 1 \text{ count}/7.53 \mu v \text{ at maximum GAIN}$$

COMBINED PACEMAKER DELTA MODULATOR AND BANDPASS FILTER

BACKGROUND OF THE INVENTION

This invention relates to pacemaker sense circuits and, more particularly, to a single-amplifier circuit which functions as both a delta modulator and a bandpass filter.

A pacemaker, whether implantable or external, typically includes a bandpass filter as part of the sense circuit. The center frequency is usually in the 30–80 Hz range, and the filter usually has a value of Q which is greater than 1. Bandpass filter designs for use in pacemaker sense circuits are well-known to those skilled in the art. It is usually required to use two capacitors and two resistors in the filter. In order to achieve a Q of 2, the preferred value (too high a value gives rise to ringing, and too low a value sacrifices gain and gives rise to poorer noise rejection), it is necessary to include an amplifier as part of the filter.

Another technique involved in sensing that has been the subject of several patents in recent years is that of delta modulation. Reference is made, for example, to U.S. Pat. Nos. 4,448,196; 4,466,440; 4,509,529 and 4,527,133.

A delta modulator, in its most basic form, requires not only a capacitor which can be charged and discharged, but also an amplifier for operating on the signal and the potential across the capacitor in order to determine whether the capacitor should be charged or discharged during the current sampling period. (There are other components, such as two current sources, which a delta modulator requires, but these other components have no bearing on the subject invention.) Taken together, a delta modulator and a bandpass filter would appear to require a total of three capacitors, two resistors and two amplifiers.

SUMMARY OF THE INVENTION

It is a general object of my invention to provide a combined delta modulator and bandpass filter for a pacemaker sense circuit in which only a single amplifier is required. The main advantage of the invention is not in the savings of components, although one less amplifier is required. The main advantage of the invention is that an implanted pacemaker, or other device whose power consumption is to be minimized, would have one less amplifier which draws current, thus extending the life of the device.

In a typical delta modulator, the input signal is applied through the capacitor to the minus input of an operational (differential) amplifier, and a reference potential is applied to the plus input. Depending on the polarity of the output of the operational amplifier during each sampling time, a current of one polarity or the other is caused to flow through the capacitor. In accordance with the principles of my invention, a similar arrangement is employed. However, instead of connecting the plus input of the amplifier to a reference potential, it is also coupled to the input signal. Furthermore, the filter components are connected across both inputs of the amplifier. It is not apparent from looking at the circuit why it functions as both a delta modulator and a bandpass filter. That it does has to be demonstrated through mathematical analysis.

BRIEF DESCRIPTION OF THE DRAWINGS

Further objects, features and advantages of the invention will become apparent upon consideration of the following detailed description in conjunction with the drawing, in which:

FIG. 4 depicts the equivalent circuit of FIG. 1 when using the transformation of FIG. 3, together with the equations which characterize its operation;

FIG. 5 depicts the input section of a sense circuit which is typically found in practice, and which precedes the illustrative embodiment of the invention shown in FIG. 1, together with the equations characterizing its operation; and FIG. 6 represents the gain of a typical bandpass filter with different values of Q, together with the final gain equation for a pacemaker sense channel which comprises in succession the circuits of FIGS. 5 and 1.

DESCRIPTION OF THE PREFERRED EMBODIMENT

Figure 1:
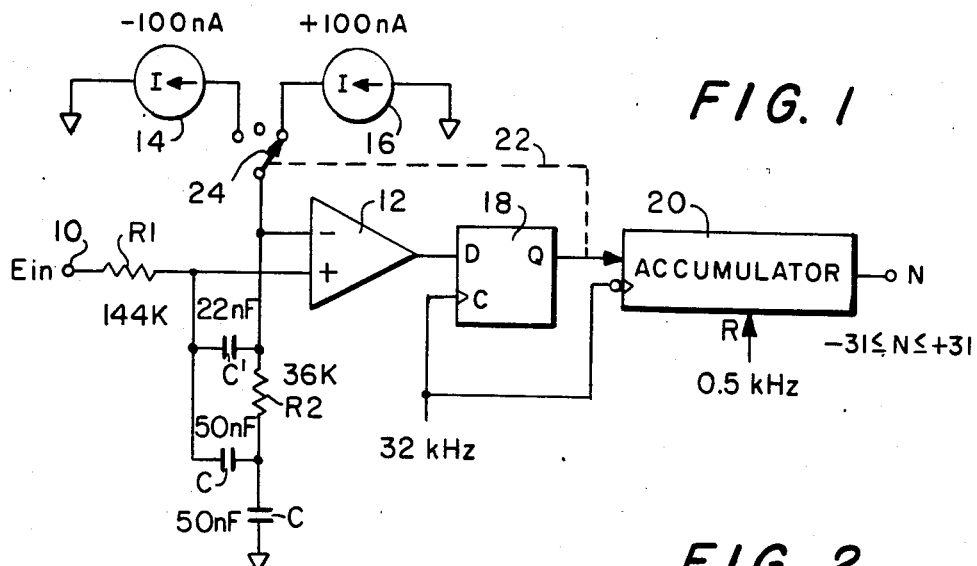
FIG. 1 depicts the illustrative embodiment of the invention.

Referring to FIG. 1, an input signal Ein is applied to terminal 10. The circuit of FIG. 1 is designed to operate on a pacemaker sense signal, although the invention is applicable to other input signals which require both bandpass filtering and delta modulation. The input signal is applied through a resistor R1 to the plus input of differential amplifier 12. Input resistence R1 can be thought of as the sum of any discrete resistor which is used and the equivalent resistance seen looking into the input signal source.

The output of differential amplifier 12 is applied to the D input of flip-flop 18. The flip-flop is clocked at a 32-kHz rate, and the Q output reflects the state of the input at the preceding clock pulse. The dashed line 22 represents control over switch 24. The switch is shown in the position in which it is maintained when the Q output of the flip-flop is high; at this time, 100nA current source 16 is connected through the switch as shown. For the opposite state of the flip-flop, it is current source 14, of the same magnitude but opposite polarity, which is connected to the switch. In the intermediate position of the switch, neither current source is connected. When current does flow, it flows through the three capacitors shown in the drawing, one of magnitude C' and two each of magnitude C. It will be noted that there are five components—the three capacitors, and resistors R1 and R2.

The operation of a delta modulator can be best understood by first considering a different circuit, one in which the input signal is applied through capacitor C' to the minus input of the comparator, as shown, but with the plus input of the comparator being connected to a reference potential and otherwise disconnected from the circuit. Suppose, for example, that the input signal starts to decrease from some quiescent level. This tends to cause the potential at the minus input of the comparator to fall, and the output of the comparator goes high. The D input of flip-flop 18 is thus high, and the next 32 kHz clock pulse causes the Q output of the flip-flop to go high. Current flows from source 16 to the left through capacitor C'. This tends to restore the potential at the minus input of the comparator to the reference level. In a similar manner, source 14 controls a left-to-right current flow through the capacitor when. the input signal increases from a quiescent level and the output of comparator 12 goes low to reset flip-flop 18. The state of the flip-flop is controlled in accordance with the current bit sample. Since the flip-flop states control current flows from respective current sources, the output of the comparator not only represents a bit sample indicative of the manner in which the input signal is changing, but it also controls the current sources as required.

The comparator minus input is a virtual ground. Capacitor C' is charged and discharged by the current sources so that the potential at the input has added to it or subtracted from it a capacitor potential such that the resulting level at the minus input of the comparator equals the reference potential at the plus input. If a steadystate condition has been achieved, with alternating 0 and 1 bit samples appearing at the flip-flop output, and then there is a sudden change in the potential at the input, a number of bit samples of the same value will be generated until the capacitor has charged or discharged to an extent which compensates for the change at the input. The number of bit samples of constant value at the output of the delta modulator thus represents the magnitude of the change in the input signal, with the value of the output bits representing the direction of the change.

Instead of connecting the plus input to a reference potential as just described, however, I connect the plus input of the comparator to the input. Also, I connect two other capacitors of magnitude C, and resistor R2, across the inputs of the comparator. Most pacemakers and sense amplifiers have a bandpass filter consisting of two capacitors and two resistors. But the typical bandpass filter also includes an amplifier. In order to achieve a filter Q value greater than 1, either inductors must be used or an amplifier and capacitors. As far as the circuit of FIG. 1 is concerned, there is no savings in passive components since a delta modulator (requiring one capacitor) and a filter (requiring two capacitors and two resistors) would still require the same number of components shown in the drawing—three capacitors and two resistors. The savings is in the use of a single amplifier, comparator 50, instead of the two which would otherwise be required—one for the delta modulator and the other for the filter. The main advantage of achieving both delta modulator and filter functions with the use of a single active device is that less power is required to operate the pacemaker.

The output of the flip-flop represents a sequence of bit values indicative of the way in which the input signal is changing. The output is applied to the data input of accumulator 20. The accumulator is also clocked at the 32-kHz rate, but on alternate phases. During each clock cycle, after the flip-flop state is established, the accumulator count is incremented or decremented depending upon the state of the flip-flop. The accumulator is reset at a 0.5 -kHz rate. During each 2-millisecond cycle of the accumulator, there are 64 clock pulses. In the illustrative embodiment of the invention, switch 24 connects neither current source to switch 24 for two clock periods of each cycle. (This allows "housekeeping" functions to be performed, such as loading a register from the accumulator, resetting the accumulator, and balancing of the current sources as disclosed in U.S. Pat. No. 4,527,133.) The flip-flop is not clocked for these two periods. Also, it is more convenient to think of the accumulator as being reset to a count N of −31, and only being incremented when it is clocked if the Q output of the flip-flop represents a 1. In such as case, the output of the accumulator, which is processed every 2 milliseconds, is always a number between the limits of −31 and +31. The pacemaker may rely on known algorithms for determining the presence of cardiac activity by processing the samples which occur at 2-millisecond intervals.

The details of the derivation and the processing of the digital samples is not important for an understanding of the present invention, although for illustrative purposes the scheme of FIG. 1 will be analyzed. For present purposes, it is sufficient to understand that during each 64-count cycle, the output N varies between −31 and +31. If a sample is zero, then the average current furnished to the minus input of amplifier 12 is zero and indicates that the Q output of the flip-flop was high fifty percent of the time. Otherwise, the sign of N indicates the polarity of the average current and the absolute magnitude of N represents its amplitude. For example, for a steadily increasing input signal, the Q output of the flip-flop will be high 100 percent of the time, and the value of N at the end of a 2-millisecond sampling interval will be +31.

Figure 2:
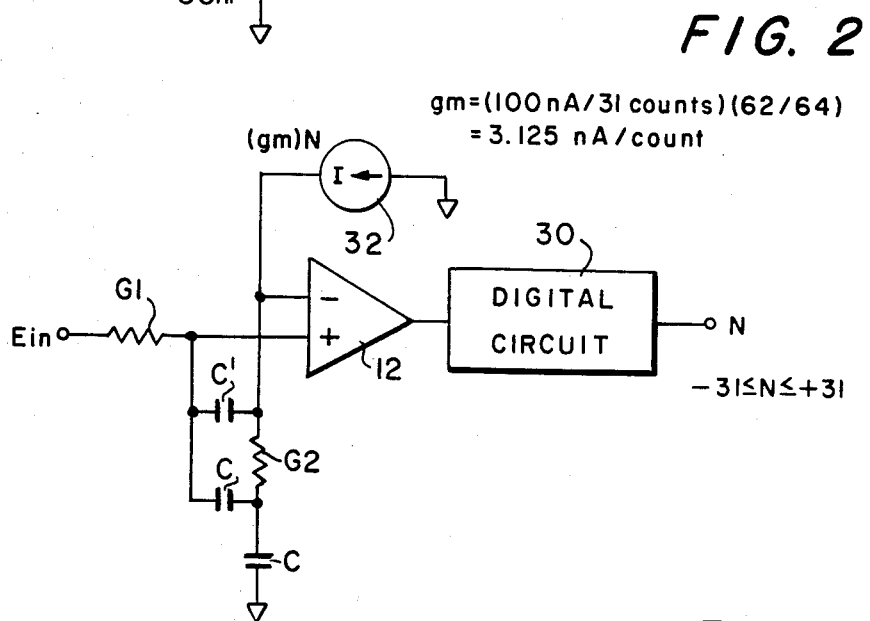
FIG. 2 depicts an equivalent circuit which will be helpful in analyzing the circuit of FIG. 1.

The illustration of FIG. 2 is a simplification of the circuit of FIG. 1. The flip-flip and accumulator are represented by "digital circuit" 30, since the details are not important. Resistors R1 and R2 are shown in admittance form. The most important simplification of the circuit of FIG. 2, however, pertains to the substitution of equivalent current source 32 for current sources 14 and 16 in FIG. 1. The drawing also shows how the gm value of current source 32 is determined, gm being the average current per count which is delivered to the minus input of the amplifier, with the total current delivered during each 64-count sampling interval being equal to (gm)N. The maximum value of N is +31 and the minimum value is −31. The corresponding average current which is caused to flow in either case has an amplitude of 100 na multiplied by 62/64 because both current sources are disconnected for 2 of every 64 clock cycles. Thus the current per count, gm, is derived as shown in FIG. 2, with the final value being 3.125 nA/count. In other words, the current is proportional to N, with a proportionality constant of 3.125. The comparator sampling frequency of 32 kHz is so much higher than the frequencies of interest in a cardiac signal that only the average current need be considered. This is because the current actually delivered, which varies in polarity, is averaged by the capacitors. (Capacitor C' plays no part in the filter analysis below, but is necessary to average the current.)

Figure 3:
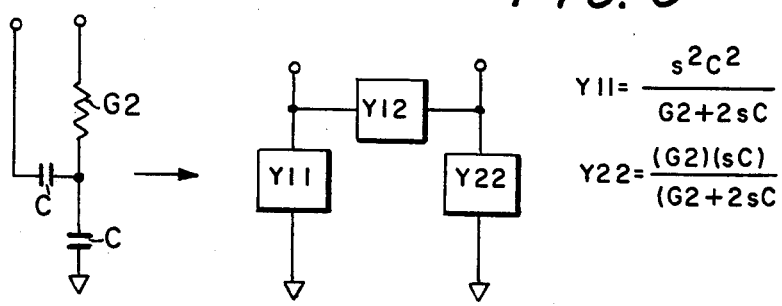
FIG. 3 illustrates a transformation which will simplify the mathematical analysis.

FIG. 3 depicts a wye-to-delta transformation, together with the applicable equations which define the admittances. In the transformation, each new admittance is the product of the two admittances across which it is connected, divided by the sum of all three admittances. The admittances Y11 and Y22 are in their Laplace Transform form. The equation for the Y12 admittance is not shown because it is not needed in the subsequent analysis. The reason that the Y12 admittance can be ignored is that it is connected, together with capacitor C' in FIG. 2, across the two inputs of the comparator 12. Because the comparator maintains zero volts, on average, between its input terminals, impedances connected across the two inputs do not draw current. (Any AC currents which are present are at frequencies much too high to be of any interest).

Substituting the admittances derived in FIG. 3 in the circuit of FIG. 2, but omitting capacitor C' and admittance Y12, gives rise to the circuit of FIG. 4. The net result of having the output of comparator 12 control the state of switch 24 in FIG. 1 is to insure that the potentials at the two inputs of the comparator are maintained equal. The first equation shown under the drawing in FIG. 4 is derived simply by equating the potentials at the two inputs. For the minus input, the potential is the current magnitude divided by the applicable admittance. For the plus input, the input Ein is multiplied by the ratio of the admittance of the input resistor to the total admittance.

The second equation included as part of FIG. 4, derived from the first equation, is for the output N, where the admittances Y11 and Y22 are replaced by the actual values shown in FIG. 3. The final value of N is in a form in which one of the denominator factors consists of the sum of two bracketed expressions.

A typical pacemaker sense circuit includes more than just that shown in F In my co-pending application, Ser No. 891,479, filed on even date herewith, what is disclosed includes not only the circuit of FIG. 1, but also a preceding operational amplifier and an attenuator. These two components are shown in FIG. 5 as blocks 40 and 42. The input signal, the actual sensed signal, is represented by Ei, and the output signal is the Ein signal shown in FIGS. 1, 2 and 4. The gain of the operational amplifier in my co-pending application is 30, and thus the output of operational amplifier 40 in FIG. 5 is shown as 30(Ei). The gain of the attenuator varies between 0 and 255/256, depending upon the word stored in a register whose individual bits control respective switches in a ladder network. The gain of the attenuator is depicted in box 42 of FIG. 5 in a form which indicates that the gain is dependent upon the magnitude of the 8-bit register word. The output signal Ein, which is the input to the circuit of FIGS. 1, 2 and 4, is simply the product of the input signal Ei and the gains of the operational amplifier and attenuator, as shown in FIG. 5.

Also shown as part of FIG. 5 is the equation for N/Ei. This quantity has units of counts per volt and represents the relationship between the final count N at the end of each 2-millisecond sampling interval and the input potential. The formula is derived by using the last equation of FIG. 4, but substituting for Ein the equivalent signal shown in FIG. 5 in terms of Ei. The equation for N/Ei is written in terms of Q and $w_o$, using the definitions given for these quantities and the actual values of the various components. The importance of the form of the equation depicted in FIGS. 4 and 5 is that the factor with the two bracketed expressions, together with the numerator sC, is the form of the equation of a bandpass filter whose center frequency is 44.2 Hz and whose value of Q is 2. This proves that the overall gain in terms of counts per volt has a second-order pole, i.e., a bandpass filter whose center frequency is perfectly suitable for filtering a pacemaker sense signal, and whose value of Q is optimal for pacemaker work. Using the same number of discrete components otherwise required for both a delta modulator and a bandpass filter, the functions of both are achieved with the use of only a single amplifier.

The curves of FIG. 6 depict gain as a function of frequency for a bandpass filter with different values of Q. As mentioned above, for pacemaker work it is most advantageous to use a filter whose value of Q is greater than 1. It is of interest to calculate the gain of the filter characterized by the equations of FIG. 5 for a sinusoidal signal whose frequency is that of the center frequency of the filter. Using the gain equation of FIG. 5, all that has to be done is to substitute jw for s. The calculation is shown in FIG. 6 and it is clear that the maximum gain of the overall channel, for a frequency of 44.2 Hz, is one count per 7.53 microvolts. [This assumes that the attenuator is set to provide a gain of 255/256.] The resolution of the channel is thus 7.53 microvolts, and a pacemaker using the component values depicted in the drawing will be capable of processing very low-magnitude signals. Empirical testing has shown that R-wave sensitivity is about 45 percent of the peak sine wave sensitivity because the energy of the R wave is spread from about 0 to 40 Hz. This means that a typical 200-microvolt peak-to-peak sense signal gives rise to a count N of (200/7.53)(0.45), or about 12.

Referring to my above-identified application, and in particular FIG. 2B thereof, the only on-chip resistor of the two depicted in FIG. 1 herein is resistor R1—the equivalent impedance seen looking into the output of the attenuator. Resistor R2 and all three capacitors are external components. Resistor R1, which because it is on-chip cannot be controlled as accurately as the other components, does not appear in the formula for the gain; it affects the gain only indirectly by changing the center frequency and the Q of the filter. What this means is that variations in on-chip components do not vary the sensitivity appreciably, and good repeatability can be obtained with the use of only one external resistor (R2) whose magnitude can be carefully controlled. Using a standard R-wave test input, resistor R1 was varied in magnitude in order to ascertain its effect on the gain. Increasing R1 by 40% resulted in a drop in the gain of only 6%, and decreasing R1 by 40% resulted in an increase in the gain of only 9%. (The center frequency dropped in the first case to 37 Hz and increased in the second to 57 Hz, while the value of Q went from 2.0 to 1.6 in the first case, and from 2.0 to 2.3 in the second.)

Although the invention has been described with reference to a particular embodiment, it is to be understood that this embodiment is merely illustrative of the application of the principles of the invention. Numerous modifications may be made therein and other arrangements may be devised without departing from the spirit and scope of the invention.

I claim:

1. A combined pacemaker delta modulator and bandpass filter comprising a differential amplifier having plus and minus inputs, means for coupling an input signal to said plus input, means for connecting an RC bandpass filter network between said plus and minus inputs, and means for periodically sampling the output of said differential amplifier and, depending upon its polarity, applying a constant current of respective polarity to said minus input.

2. A combined pacemaker delta modulator and bandpass filter in accordance with claim 1 wherein said RC bandpass filter network includes two resistors and three capacitors.

3. A combined pacemaker delta modulator and bandpass filter in accordance with claim 1 wherein the effective bandpass filter has a value of Q greater than 1 and a center frequency in the range 30–80 Hz.

4. A combined delta modulator and bandpass filter comprising a differential amplifier having two inputs, means for coupling an input signal to a first of said inputs, means for connecting an RC bandpass filter network between said two inputs, and means for periodically sampling the output of said differential amplifier and, depending upon its polarity, applying a constant current of respective polarity to the second of said inputs.

5. A combined delta modulator and bandpass filter in accordance with claim 4 wherein said RC bandpass filter network includes two resistors and three capacitors.

6. A combined pacemaker delta modulator and bandpass filter in accordance with claim 5 wherein the effective bandpass filter has a value of Q greater than 1.

7. A sense circuit comprising a single differential amplifier, capacitor means for coupling an input sense signal to a first input of said amplifier, means for coupling said input sense signal directly to a second input of said amplifier, means for periodically sampling the output of said amplifier and, depending upon its polarity, applying a constant current of respective polarity to said capacitor means, and filter means connected to said first and second inputs for causing said amplifier to operate as a second-order bandpass filter.

* * * * *